(12) United States Patent
Marciano et al.

(10) Patent No.: US 10,854,316 B2
(45) Date of Patent: Dec. 1, 2020

(54) METHODS AND SYSTEMS FOR PREDICTION OF A DNA PROFILE MIXTURE RATIO

(71) Applicants: Michael Marciano, Manlius, NY (US); Jonathan D. Adelman, Mexico, NY (US); Laura C. Haarer, Jamesville, NY (US)

(72) Inventors: Michael Marciano, Manlius, NY (US); Jonathan D. Adelman, Mexico, NY (US); Laura C. Haarer, Jamesville, NY (US)

(73) Assignee: Syracuse University, Syracuse, NY (US)

( * ) Notice: Subject to any disclaimer, the term of this patent is extended or adjusted under 35 U.S.C. 154(b) by 412 days.

(21) Appl. No.: 15/367,814

(22) Filed: Dec. 2, 2016

(65) Prior Publication Data
US 2017/0161431 A1   Jun. 8, 2017

Related U.S. Application Data

(60) Provisional application No. 62/262,610, filed on Dec. 3, 2015.

(51) Int. Cl.
*G16B 30/00* (2019.01)
*G16B 40/00* (2019.01)

(52) U.S. Cl.
CPC .............. *G16B 30/00* (2019.02); *G16B 40/00* (2019.02)

(58) Field of Classification Search
CPC ........ G16B 20/00; G16B 30/00; G16B 40/00; G16B 25/00; G16B 5/00; G16B 20/10; G16B 30/10; G16B 20/20; G16B 40/10; G16B 40/20; G16H 10/60; G16H 40/63; G16H 50/20; G06F 19/00; G06F 16/00; G06F 16/285; G06F 17/10; G06F 17/11;
(Continued)

(56) References Cited

U.S. PATENT DOCUMENTS

| 8,898,021 B2 * | 11/2014 | Perlin | C12Q 1/6851 702/19 |
| 2010/0086926 A1 * | 4/2010 | Craig | G16B 20/00 435/6.1 |

FOREIGN PATENT DOCUMENTS

WO   2017/096219   *   1/2017

OTHER PUBLICATIONS

Benschop et al. LoCIM-tool: an experts assistant for inferring the major contributor's alleles in mixed consensus DNA profiles. 2014 Forensic Science International: Genetics vol. 11, pp. 154-163.*

(Continued)

*Primary Examiner* — Mary K Zeman
(74) *Attorney, Agent, or Firm* — Bond Schoeneck and King PLLC; David Nocilly

(57) ABSTRACT

A system configured to characterize a ratio of contributors to a DNA mixture within a sample, the system including: a sample preparation module configured to generate initial data about the DNA mixture within the sample; a processor comprising a ratio of contributors determination module configured to: (i) receive the generated initial data; (ii) analyze the generated initial data to determine the ratio of contributors to the DNA mixture within the sample; and an output device configured to receive the determined ratio of contributors from the processor, and further configured to output information about the received determined ratio of contributors.

10 Claims, 3 Drawing Sheets

(58) Field of Classification Search
CPC ..... G06F 17/00; G06F 7/00; C12Q 2537/165; C12Q 1/6809; C12Q 2600/156; C12Q 2537/16; C12Q 2600/172; C12Q 1/6827; G01R 33/4625; G01R 33/465; A61B 5/7203; A61B 5/7264; A61B 5/7267
See application file for complete search history.

(56) References Cited

OTHER PUBLICATIONS

Mitchell, A. A. et al. Validation of a DNA mixture statistics tool incorporating allelic drop out and drop in. Forensic Science International: Genetics vol. 6 2012 pp. 749-761.*
Benschop et al. The effect of varying the number of contributors on likelihood ratios for complex DNA mixtures. 2015 Forensic Science International: Genetics, vol. 19 p. 92-99.*
Anderson, M. M. Identifying the most likely contributors to a Y-STR mixture using the discrete Laplace method. Forensic Science International: Genetics 2015, vol. 15, pp. 76-83.*
Westen, A. A. et al. Tri-allelic SNP markers enable analysis of mixed and degraded DNA samples. Forensic Science International: Genetics 2009 vol. 3 pp. 233-241.*
Marciano, M. A. PACE: probabilistic assessment for contributor estimation—a machine learning-based assessment of the number of contributors in DNA mixtures. Forensic Science International: Genetics 2017 vol. 27, pp. 82-91.*
Perez, J. et al. Estimating the number of contributors to two- three-, and four-person mixtures containing DNA in high template and low template amounts. Croatian Medical Journal (2011) vol. 52 No. 3 pp. 314-326.*

* cited by examiner

METHODS AND SYSTEMS FOR PREDICTION OF A DNA PROFILE MIXTURE RATIO

CROSS-REFERENCE TO RELATED APPLICATION

This application claims priority to U.S. Provisional Patent Application Ser. No. 62/262,610, filed on Dec. 3, 2015 and entitled "Methods and Systems for Prediction of a DNA Profile Mixture Ratio," the entire disclosure of which is incorporated herein by reference.

GOVERNMENT FUNDING

This invention was made with Government support under Grant Numbers 2014-DN-BX-K029, awarded by the National Institute of Justice. The United States Government has certain rights in the invention.

FIELD OF THE INVENTION

The present disclosure is directed generally to methods and systems for identifying nucleic acid in a sample and, more particularly, to methods and systems for determining the ratio of contributors within a DNA mixture.

BACKGROUND

At the core of the genetic identification field, particularly in regard to forensic applications and clinical/medical research, is the challenge of DNA mixture interpretation. A DNA sample mixture can be defined as a mixture of two or more biological samples, and mastery of their interpretation can greatly impact the course of criminal investigations and/or quality of intelligence. The ability to identify the ratio of the contributors in a DNA sample may substantial improve the ability to identify the individual contributors within a mixed DNA sample.

Although historically expert systems have been in use for this problem, they often fail to meet the needs of the community, and there is continued demand by forensic communities for reliable methods of automation for mixture interpretation. The present state-of-the-art in DNA mixture interpretation includes expert systems which often have limited use, primarily focusing on improving the timeliness of analysis performed by forensic analysts. These systems capture the computational aspects of mixture analysis without taking more subjective factors into account. Further, these systems are used for simple mixtures, typically of two individuals (and thus low complexity). Although more advanced systems capable of analyzing 3-4 individual mixtures exist, these systems are both time- and cost-prohibitive.

For example, current methods to estimate the ratio of contributors in a mixed DNA sample rely on those DNA markers with the maximum number of alleles (or maximum number of alleles—1) given the number of contributors. These DNA markers have inherent variability where ratios at several loci within a sample may differ due to the size of the allele, locus base pair size, amount of degradation present, stochastic effects etc. These ratios are then used as a standard to help in the identification of the individual components or contributors in a DNA profile at those loci where a ratio cannot be determined. The calculation of these ratios is typically performed manually using a standard scientific calculator.

Accordingly, there is a need in the art for methods and systems that perform complicated DNA mixture interpretation, particularly with regard to more accurately determining the ratio of contributors within a DNA mixture.

SUMMARY OF THE INVENTION

The present disclosure is directed to methods and systems for determining the ratio of contributors within a DNA mixture. The ratio of contributors within a DNA mixture is the one of the key metrics used to separate the individual contributors during mixture deconvolution. The ratio is typically calculated using simple mathematical operations and based on known biological phenomena such as genetic dosage. This method, although effective, is limited by the capacity of human computation and fails to utilize much of the information contained within the profile.

Accordingly, the methods and systems described herein combine statistical and biological approaches which are made feasible through a processor. According to an embodiment, the system includes a combinatorial algorithm to enumerate all potential DNA mixture scenarios within a single DNA marker. The system further includes an outlier removal algorithm, and a clustering algorithm to identify the most similar ratios among DNA markers.

According to one aspect is a method for determining a ratio of the proportion of DNA from each contributor within a mixed DNA sample, comprising the steps of: (i) characterizing a parameter of the DNA mixture; (ii) characterizing a plurality of markers within the DNA mixture; (iii) identifying which of the plurality of markers exhibits a maximum number of alleles, wherein at least one of the plurality of markers is identified; (iv) enumerating, based on the identification, all possible scenarios for contributors to the DNA mixture; (v) determining a mixture ratio for each enumerated scenario, wherein every allele found in a given marker must be represented in the scenario; (vi) identifying all possible clusters for the determined mixture ratios, wherein a cluster is a group of ratios comprising just one ratio from the at least one identified marker; (vii) removing any statistical outliers from each of the identified clusters; (viii) identifying candidate clusters, wherein a cluster is identified as a candidate if the variance of the distance from each mixture ratio to the cluster's centroid is below a certain user-specified threshold; and (ix) comparing all of the candidate clusters to all the of the mixture ratios, wherein the candidate ratio with the highest number of markers containing at least one similar ratio at each marker is identified as the DNA profile mixture ratio.

According to an embodiment, the method further includes the step of characterizing a parameter of the DNA mixture.

According to an embodiment, the method further includes the step of characterizing the plurality of markers within the DNA mixture.

According to an embodiment, the method further includes the step of preparing the sample for analysis.

According to a second aspect is a system configured to characterize a ratio of contributors to a DNA mixture within a sample. The system includes: a sample preparation module configured to generate initial data about the DNA mixture within the sample; a processor comprising a ratio of contributors determination module, the ratio of contributors determination module configured to: (i) receive the generated initial data; (ii) analyze the generated initial data to determine the ratio of contributors to the DNA mixture within the sample; and an output device configured to receive the determined ratio of contributors from the processor, and further configured to output information about the received determined ratio of contributors.

According to an embodiment, the output device comprises a monitor.

According to an embodiment, the sample preparation module comprises amplification of DNA within the sample. According to an embodiment, the sample preparation module comprises amplification of one or more DNA markers within the sample.

According to an embodiment, analyzing the generated initial data to determine the ratio of contributors to the DNA mixture comprises the steps of: (i) identifying which of a plurality of markers within the DNA mixture exhibit a maximum number of alleles; (ii) enumerating, based on the identification, all possible scenarios for contributors to the DNA mixture; (iii) determining a mixture ratio for each enumerated scenario; (iv) identifying all possible clusters for the determined mixture ratios; (v) removing any statistical outliers from each of the identified clusters; (vi) identifying candidate clusters, wherein a cluster is identified as a candidate if the variance of the distance from each mixture ratio to the cluster's centroid is below a certain threshold; and (vii) comparing all of the candidate clusters to all the of the mixture ratios, wherein the candidate ratio with the highest number of markers containing at least one similar ratio at each marker is identified as the DNA profile mixture ratio.

According to a second aspect is a system configured to characterize a ratio of contributors to a DNA mixture within a sample. The system includes a processor configured to receive data about the DNA within the sample, and further configured to perform the steps of: identifying, using the received data, which of a plurality of markers within the DNA mixture exhibit a maximum number of alleles, or the maximum minus one, wherein at least one of the plurality of markers is identified; enumerating, based on the identification, all possible scenarios for contributors to the DNA mixture; determining a mixture ratio for each enumerated scenario, wherein every allele for the at least one identified marker is represented in the mixture ratio; identifying all possible clusters for the determined mixture ratios, wherein a cluster is a group of ratios comprising just one ratio from the at least one identified marker; removing any statistical outliers from each of the identified clusters; identifying candidate clusters, wherein a cluster is identified as a candidate if the variance of the distance from each mixture ratio to the cluster's centroid is below a certain threshold; and comparing all of the candidate clusters to all the of the mixture ratios, wherein the candidate ratio with the highest number of markers containing at least one similar ratio at each marker is identified as the DNA profile mixture ratio.

These and other aspects of the invention will be apparent from the embodiments described below.

BRIEF DESCRIPTION OF THE DRAWINGS

The present invention will be more fully understood and appreciated by reading the following Detailed Description in conjunction with the accompanying drawings, in which.

DETAILED DESCRIPTION OF EMBODIMENTS

There is a continued need for methods and systems that perform DNA mixture interpretation in both a time-effective and cost-effective manner. Accordingly, the present disclosure is directed to methods and systems for determining the ratio of contributors within a DNA mixture, namely by combining statistical and biological approaches. According to an embodiment, the method and system enumerates all potential DNA mixture scenarios within a single DNA marker, removes outliers, and clusters the results to identify the most similar ratios among DNA markers.

Figure 1:
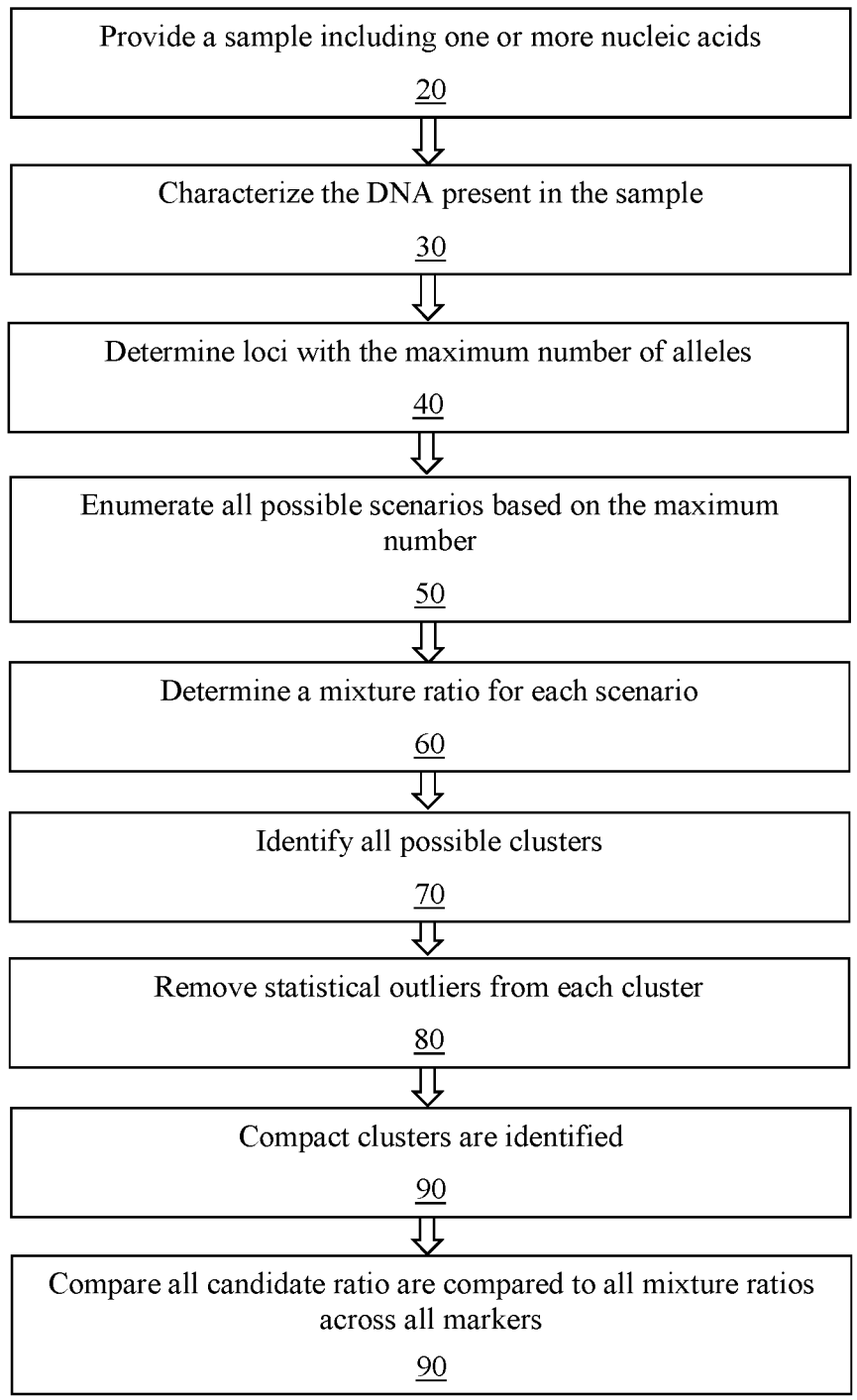
FIG. 1 is a flowchart of a method for DNA mixture analysis, in accordance with an embodiment.

Referring to FIG. 1 is a flowchart of a method 10 for DNA mixture analysis in accordance with an embodiment. At step 20, a sample is provided. The sample can previously be known to include a mixture of DNA from two or more individuals, for example. Alternatively, the sample can be obtained from a location or source that is suspected of containing DNA from two or more individuals. As yet another alternative, the sample can be obtained from a location or source where it is merely possible that it could contain DNA from two or more individuals. The sample can be obtained directly in the field and then analyzed, or can be obtained at a distant location and/or time prior to analysis. Any sample that could possibly contain DNA therefore could be utilized in the analysis. According to another embodiment, the sample contains a mixture of DNA from two or more species.

At step 30, a parameter of all or part of the DNA in the sample—if DNA is present in the sample—is characterized. For example, the sample may be processed, such as by a DNA extraction and/or separation or purification step, prior to analysis. Alternatively, the sample may be analyzed without a processing step. DNA present in the sample can be characterized by, for example, capillary electrophoresis based fragment analysis, sequencing using PCR analysis with species-specific and/or species-agnostic primers, SNP analysis, one or more loci from human Y-DNA, X-DNA, and/or atDNA, or any other of a wide variety of DNA characterization methods. According to a preferred embodiment, the DNA ratio characterization step results in one or more data files containing DNA sequence and/or loci information that can be utilized for identification of one or more sources of the DNA in the sample, either by species or individually within a species (such as a particular human being, etc.). According to advanced methods, other characteristics of the DNA may be analyzed, such as methylation patterns or other epigenetic modifications, among other characteristics.

At step 40 of the method, the system determines which DNA markers or loci exhibit the maximum number of alleles, or the maximum number of allele minus 1, in the DNA mixture.

At step 50 of the method, the system enumerates all possible scenarios based on the determined maximum number of alleles, where a scenario is a combination of possible allele pairs/contributors.

At step 60 of the method, the system determines a mixture ratio for each valid scenario, where every allele in the marker is represented. A scenario is considered valid if every allele appearing in a given marker appears at least once in said scenario.

At step 70 of the method, the system identifies all possible clusters, where clusters are a group of ratios containing one, and only one, ratio from each of the identified markers (i.e., the DNA markers or loci exhibiting the maximum number of alleles, or the maximum number of allele minus 1, in the DNA mixture).

At step 80 of the method, statistical outliers are removed from each cluster. According to an embodiment, the statistical outliers are removed from each cluster using Chebyshev's Inequality, although many other methods are possible.

At step 90 of the method, sufficiently compact clusters are identified, where compactness is the variance of the distances of each component (mixture ratio) to the cluster's centroid. The centroid represents a candidate profile mixture ratio.

At step 100 of the method, all candidate ratios are subsequently compared to all mixture ratios across all markers. The candidate ratio with the highest number of markers containing at least one similar ratio at each marker is identified as the DNA profile mixture ratio. Similarity is defined as a measure of Euclidean distance below a dynamic, user specified threshold.

Figure 2:
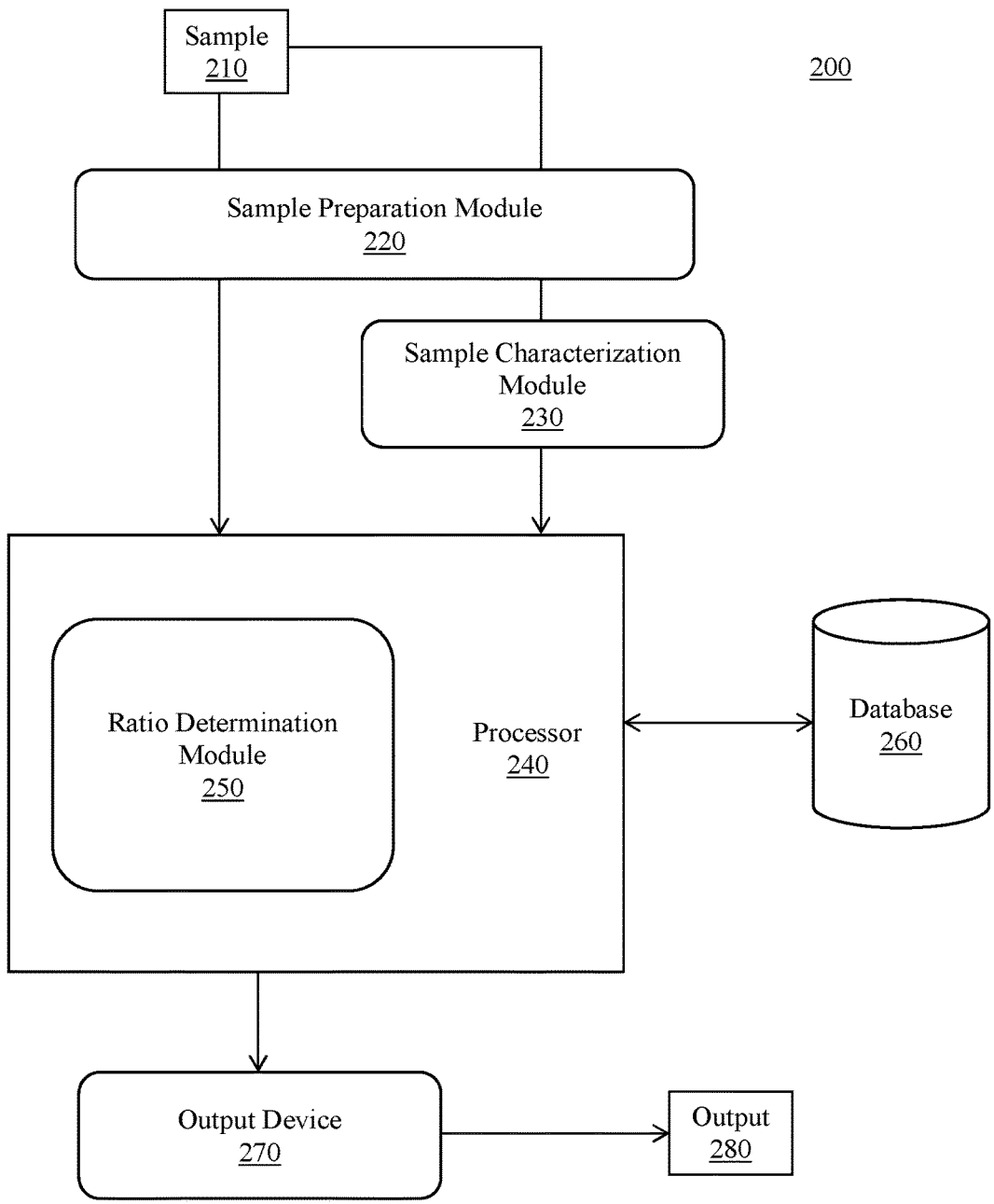
FIG. 2 is a schematic representation of a system for DNA mixture analysis, in accordance with an embodiment.

Referring to FIG. 2, in one embodiment, is a system 200 for characterizing the ratio of contributors within a DNA mixture of a sample 210, where sample 210 potentially contains DNA from one or more sources. Sample 210 can previously be known to include a mixture of DNA from two or more sources, or can be an uncharacterized sample. Sample 210 can be obtained directly in the field and then analyzed, or can be obtained at a distant location and/or time prior to analysis. Any sample that could possibly contain DNA therefore could be utilized in the analysis.

According to an embodiment, system 200 can comprise a sample preparation module 220. Sample preparation module 220 can be, for example, a device, step, component, or system that prepares the obtained sample for analysis. For example, sample preparation module 220 may comprise DNA isolation, extraction, separation, and/or purification. According to an embodiment, sample preparation module 220 may include any modification of the sample to prepare that sample for analysis.

According to an embodiment, system 200 can optionally comprise a sample characterization module 230. For example, DNA present in the sample can be characterized by, for example, capillary electrophoresis based fragment analysis, sequencing using PCR analysis with species-specific and/or species-agnostic primers, SNP analysis, one or more loci from human Y-DNA, X-DNA, and/or atDNA, or any other of a wide variety of DNA characterization methods. According to advanced methods, other characteristics of the DNA may be analyzed, such as methylation patterns or other epigenetic modifications, among other characteristics. According to an embodiment, the DNA ratio characterization step results in one or more data files containing DNA sequence and/or loci information that can be utilized for identification of one or more sources of the DNA in the sample, either by species or individually within a species (such as a particular human being, etc.).

According to an embodiment, system 200 comprises a processor 240. Processor 240 can comprise, for example, a general purpose processor, an application specific processor, or any other processor suitable for carrying out the processing steps as described or otherwise envisioned herein. According to an embodiment, processor 240 may be a combination of two or more processors. Processor 240 may be local or remote from one or more of the other components of system 240. For example, processor 240 might be located within a lab, within a facility comprise multiple labs, or at a central location that services multiple facilities. According to another embodiment, processor 240 is offered via a software as a service. One of ordinary skill will appreciate that non-transitory storage medium may be implemented as multiple different storage mediums, which may all be local, may be remote (e.g., in the cloud), or some combination of the two.

According to an embodiment, processor 240 comprises or is in communication with a non-transitory storage medium 260. Database 260 may be any storage medium suitable for storing program code for executed by processor 240 to carry out any one of the steps described or otherwise envisioned herein. Non-transitory storage medium may be comprised of primary memory, secondary memory, and/or a combination thereof. As described in greater detail herein, database 260 may also comprise stored data to facilitate the analysis, characterization, and/or identification of the DNA in the sample 210.

According to an embodiment, processor 240 comprises a ratio determination algorithm or module 250. Ratio determination algorithm or module 250 may be configured to comprise, perform, or otherwise execute any of the functionality described or otherwise envisioned herein. According to an embodiment, ratio determination algorithm or module 250 receives data about the DNA within the sample 210, among other possible data, and utilizes that data to determine or estimate the ratio of contributors within the DNA of the sample, among other outcomes.

According to an embodiment, system 200 comprises an output device 270, which may be any device configured to or capable of generating and/or delivering output 280 to a user or another device. For example, output device 270 may be a monitor, printer, or any other output device. The output device 270 may be in wired and/or wireless communication with processor 240 and any other component of system 200. According to yet another embodiment, the output device 270 is a remote device connected to the system via a network. For example, output device 270 may be a smartphone, tablet, or any other portable or remote computing device. Processor 240 is optionally further configured to generate output deliverable to output device 270, and/or to drive output device 270 to generate and/or provide output 280. As described herein, output 280 may comprise information about the ratio of contributors to the DNA found in the sample, and/or any other received and/or derived information about the sample.

Figure 3:
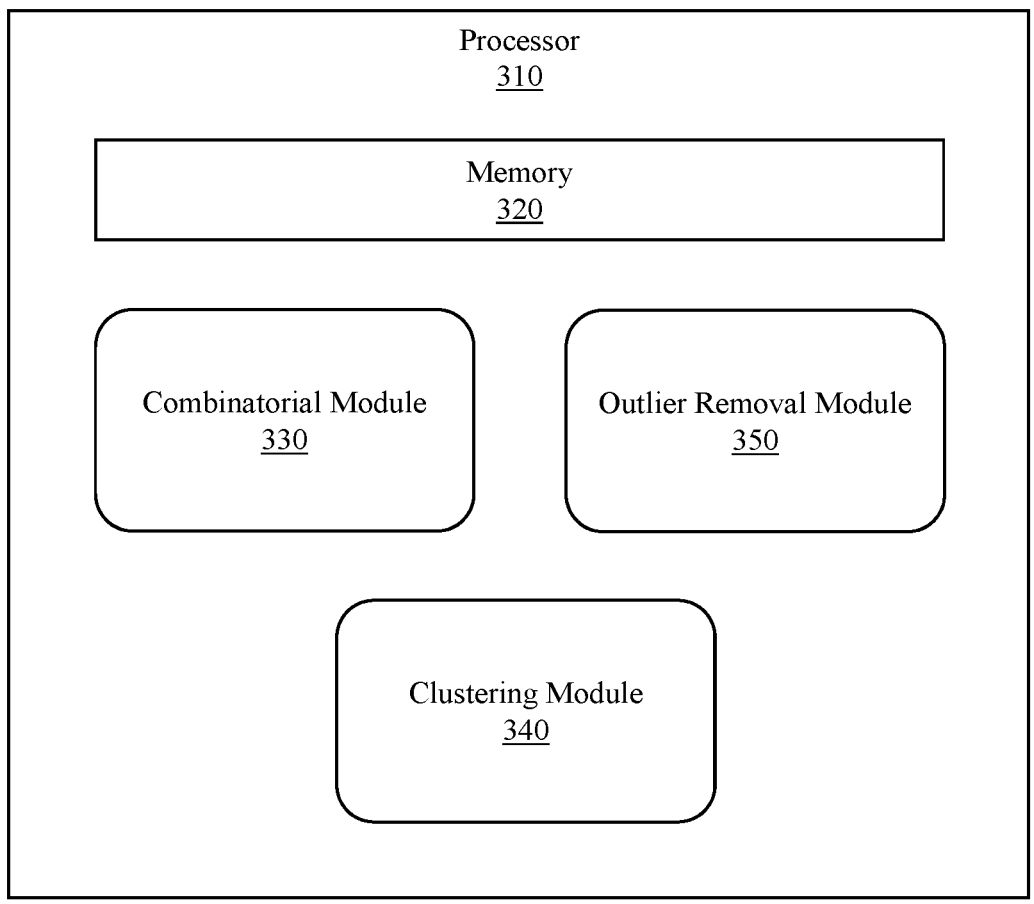
FIG. 3 is a schematic representation of a system for DNA mixture analysis, in accordance with an embodiment.

Referring to FIG. 3, in one embodiment, is a system 300 for characterizing the ratio of contributors within a DNA mixture of a sample, where the sample potentially contains DNA from one or more sources. The sample can previously be known to include a mixture of DNA from two or more sources, or can be an uncharacterized sample. The sample can be obtained directly in the field and then analyzed, or can be obtained at a distant location and/or time prior to analysis. Any sample that could possibly contain DNA therefore could be utilized in the analysis.

According to an embodiment, system 300 comprises a processor 310. Processor 310 can comprise, for example, a general purpose processor, an application specific processor, or any other processor suitable for carrying out the processing steps as described or otherwise envisioned herein. According to an embodiment, processor 310 may be a combination of two or more processors. Processor 310 may be local or remote from one or more of the other components of system 310. For example, processor 310 might be located within a lab, within a facility comprise multiple labs, or at a central location that services multiple facilities. According to another embodiment, processor 310 is offered via a software as a service. One of ordinary skill will appreciate that non-transitory storage medium may be implemented as multiple different storage mediums, which may all be local, may be remote (e.g., in the cloud), or some combination of the two.

According to an embodiment, processor 310 comprises a non-transitory storage medium 320. Storage medium 320 may be any storage medium suitable for storing program code for executed by processor 310 to carry out any one of the steps described or otherwise envisioned herein. Non-transitory storage medium may be comprised of primary memory, secondary memory, and/or a combination thereof. As described in greater detail herein, Storage medium 320 may also comprise stored data to facilitate the analysis, characterization, and/or identification of the DNA in the sample.

According to an embodiment, processor 310 comprises a combinatorial module 330. Combinatorial module 330 enumerates all potential DNA mixture scenarios within a single DNA marker. According to an embodiment, one or more markers within a DNA mixture are characterized. The system determines which of the plurality of markers exhibits a maximum number of alleles, and then enumerates, based on that identified marker, all possible scenarios for contributors to the DNA mixture. The system then determines a mixture ratio for each enumerated scenario, where every allele found in a given marker must be represented in the scenario.

According to an embodiment, processor 310 comprises a clustering module 340. Clustering module 340 uses the plurality of mixture ratios generated by the combinatorial module 330 to identify all possible clusters for the determined mixture ratios, where a cluster is a group of ratios comprising just one ratio from the at least one identified marker.

According to an embodiment, processor 310 comprises an outlier removal module 350. Outlier removal module 350 removes any statistical outliers from each of the possible clusters generated by the clustering module 340.

The system then identifies candidate clusters, where a cluster is identified as a candidate if the variance of the distance from each mixture ratio to the cluster's centroid is below a certain user-specified threshold. Lastly, the system compares all of the candidate clusters to all the mixture ratios, and the candidate ratio with the highest number of markers containing at least one similar ratio at each marker is identified as the DNA profile mixture ratio.

According to one embodiment, the system can comprise a single unit with one or more modules, or may comprise multiple modules in more than one location that may be connected via a wired and/or wireless network connection. Alternatively, information may be moved by hand from one module to another. The system may be implemented by hardware and/or software, including but not limited to a processor, computer system, database, computer program, and others. The hardware and/or software can be implemented in different systems or can be implemented in a single system.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

A "module" or "component" as may be used herein, can include, among other things, the identification of specific functionality represented by specific computer software code of a software program. A software program may contain code representing one or more modules, and the code representing a particular module can be represented by consecutive or non-consecutive lines of code.

As will be appreciated by one skilled in the art, aspects of the present invention may be embodied/implemented as a computer system, method or computer program product. The computer program product can have a computer processor or neural network, for example, that carries out the instructions of a computer program. Accordingly, aspects of the present invention may take the form of an entirely hardware embodiment, an entirely software embodiment, and entirely firmware embodiment, or an embodiment combining software/firmware and hardware aspects that may all generally be referred to herein as a "circuit," "module," "system," or an "engine." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowcharts/block diagrams in the Figures illustrate the architecture, functionality, and operation of possible implementations of systems, methods, and computer program products according to various embodiments of the present invention. In this regard, each block in the flowcharts/block diagrams may represent a module, segment, or portion of code, which comprises instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for characterizing a ratio of contributors to a DNA mixture within a sample, the method comprising the steps of:
   obtaining a forensic DNA sample mixture having a plurality of contributors;
   characterizing the forensic DNA sample mixture to obtain a data file containing DNA sequence data representing a plurality of markers within the forensic DNA sample mixture;
   identifying which of the plurality of markers within the forensic DNA sample mixture exhibit a maximum number of alleles, or the maximum minus one, wherein each of the plurality of markers that exhibits the maximum number of alleles is identified;
   enumerating, based on the identification, all possible scenarios for contributors to the forensic DNA sample mixture based on the determined maximum number of alleles;
   determining whether each possible scenario is valid based on whether the possible scenario has every allele appearing in one of the plurality of markers appears at least once;
   determining an initial mixture ratio for each valid scenario where every allele is represented;
   identifying all possible clusters for the determined initial mixture ratios, wherein a cluster is a group of the initial mixture ratios comprising just one ratio from each of the plurality of markers that were identified;
   removing any statistical outliers from each of the identified clusters using Chebyshev's Inequality;
   identifying candidate compact clusters, wherein a compact cluster is identified as a candidate if the variance of the distance from each mixture ratio to a centroid of the compact cluster is below a certain threshold, wherein the centroid of each compact cluster represents a candidate ratio; and
   comparing all of the candidate ratios to all the of the mixture ratios across all of the plurality of markers;
   identifying, using Euclidean distance below a dynamic threshold, the candidate ratio with the highest number of markers containing at least one similar ratio at each marker as representing the DNA profile mixture ratio that is the ratio of contributors to the forensic DNA sample mixture.

2. The method of claim 1, further comprising the step of characterizing a parameter of the forensic DNA sample mixture.

3. The method of claim 1, further comprising the step of characterizing the plurality of markers within the forensic DNA sample mixture.

4. The method of claim 1, further comprising the step of preparing the sample for analysis.

5. A system configured to characterize a ratio of contributors to a DNA mixture within a sample, the system comprising a processor configured to receive data about the DNA within the sample, and further configured to perform the steps of:
   identifying, using DNA sequence data representing a plurality of markers within the forensic DNA sample mixture within the received data, which of the plurality of markers within the DNA mixture exhibit a maximum number of alleles, or the maximum minus one, wherein each of the plurality of markers that exhibits the maximum number of alleles is identified;
   enumerating, based on the identification, all possible scenarios for contributors to the DNA mixture based on the determined maximum number of alleles;
   determining whether each possible scenario is valid based on whether the possible scenario has every allele appearing in one of the plurality of markers appears at least once;
   determining an initial mixture ratio for each valid scenario where every allele is represented;
   identifying all possible clusters for the determined initial mixture ratios, wherein a cluster is a group of the initial mixture ratios comprising just one ratio from each of the plurality of markers that were identified;
   removing any statistical outliers from each of the identified clusters using Chebyshev's Inequality;
   identifying compact clusters, wherein a compact cluster is identified as a candidate if the variance of the distance from each mixture ratio to a centroid of the compact cluster is below a certain threshold, wherein the centroid of each compact cluster represents a candidate ratio; and
   comparing all of the candidate ratios to all the of the mixture ratios across all of the plurality of markers;
   identifying, using Euclidean distance below a dynamic threshold, the candidate ratio with the highest number of markers containing at least one similar ratio at each marker as representing the DNA profile mixture ratio that is the ratio of contributors to the forensic DNA sample mixture.

6. The system of claim 5, further configuring a sample preparation module configured to generate the data about the DNA within the forensic DNA sample mixture.

7. The system of claim 6, wherein the sample preparation module comprises amplification of DNA within the forensic DNA sample mixture.

8. The system of claim 6, wherein the sample preparation module comprises amplification of one or more DNA markers within the forensic DNA sample mixture.

9. The system of claim 5, further comprising an output device configured to receive the determined ratio of contributors from the processor, and further configured to output information about the received determined ratio of contributors.

10. The system of claim 9, wherein the output device comprises a monitor.

* * * * *